(12) United States Patent
Frazee et al.

(10) Patent No.: US 10,213,898 B2
(45) Date of Patent: Feb. 26, 2019

(54) METHOD FOR DETECTING AND/OR PREVENTING GRIND BURN

(71) Applicant: Allison Transmission, Inc., Indianapolis, IN (US)

(72) Inventors: Elizabeth Frazee, Avon, IN (US); Paul Horvath, Brownsburg, IN (US)

(73) Assignee: ALLISON TRANSMISSION, INC., Indianapolis, IN (US)

( * ) Notice: Subject to any disclaimer, the term of this patent is extended or adjusted under 35 U.S.C. 154(b) by 355 days.

(21) Appl. No.: 14/875,783

(22) Filed: Oct. 6, 2015

(65) Prior Publication Data

US 2016/0025647 A1 Jan. 28, 2016

Related U.S. Application Data

(62) Division of application No. 13/958,814, filed on Aug. 5, 2013, now abandoned, which is a division of
(Continued)

(51) Int. Cl.
*B24B 49/12* (2006.01)
*B23F 23/12* (2006.01)
(Continued)

(52) U.S. Cl.
CPC ............ *B24B 49/105* (2013.01); *B23F 23/12* (2013.01); *B23F 23/1218* (2013.01);
(Continued)

(58) Field of Classification Search
CPC .............................. B24B 49/12; B23F 23/1218
(Continued)

(56) References Cited

U.S. PATENT DOCUMENTS 2,614,368 A * 10/1952 Polk .................. B24B 17/04
356/392
2,778,394 A * 1/1957 Schubert ............. B23D 61/026
144/223
(Continued)

FOREIGN PATENT DOCUMENTS

JP 59152061 A 8/1984
KR 102006057900 A 5/2006

OTHER PUBLICATIONS

Dotto, Fabio R.L. et al.; "Methodology for Automatic Selection of Passes in Surface Grinding"; Journal of the Braz. Soc. of the Mech. Sci. & Eng.; Pub. 2007 ("the Dotto Publication").
(Continued)

*Primary Examiner* — Monica Carter
*Assistant Examiner* — Marcel Dion
(74) *Attorney, Agent, or Firm* — Taft Stettinius & Hollister LLP; Stephen F. Rost

(57) ABSTRACT

The present disclosure provides a method of detecting and preventing grind burn from developing on a gear. The method includes performing acoustic emission testing while the gear is being ground during a grinding operation. The grinding wheel is evaluated during an eddy current test to detect material buildup on the grinding wheel which could cause grind burn. In addition, the method includes collecting swarf from the gear during the grinding operation and inspecting the swarf for an indication of grind burn.

13 Claims, 11 Drawing Sheets

Related U.S. Application Data application No. 13/617,804, filed on Sep. 14, 2012, now Pat. No. 8,597,075, which is a division of application No. 12/633,243, filed on Dec. 8, 2009, now Pat. No. 8,353,739.

(51) Int. Cl.

| | | |
|---|---|---|
| *B24B 49/10* | (2006.01) | |
| *B24B 19/00* | (2006.01) | |
| *G01B 11/06* | (2006.01) | |
| *G01N 21/88* | (2006.01) | |
| *G01N 27/02* | (2006.01) | |
| *G01N 27/90* | (2006.01) | |

(52) U.S. Cl.
CPC ............ *B24B 19/009* (2013.01); *B24B 49/12* (2013.01); *G01B 11/06* (2013.01); *G01M 13/021* (2013.01); *G01N 21/8806* (2013.01); *G01N 27/025* (2013.01); *G01N 27/9026* (2013.01)

(58) Field of Classification Search
USPC .......... 356/402; 73/863, 863.23, 864; 451/6, 451/47, 453
See application file for complete search history.

(56) References Cited

U.S. PATENT DOCUMENTS

| | | | |
|---|---|---|---|
| 3,517,460 A | 6/1970 | Kane et al. | |
| 3,810,002 A | 5/1974 | Sata | |
| 4,063,644 A * | 12/1977 | Hoffman | G01N 21/91 205/791 |
| 4,169,677 A | 10/1979 | Luria | |
| 4,438,598 A | 3/1984 | Wohlmuth | |
| 4,495,587 A | 1/1985 | Plante et al. | |
| 4,514,934 A | 5/1985 | Ray et al. | |
| 4,744,348 A | 5/1988 | Oda et al. | |
| 4,961,287 A * | 10/1990 | Compton | B24B 3/38 451/193 |
| 4,998,957 A | 3/1991 | Youden | |
| 5,125,188 A | 6/1992 | Ogawa et al. | |
| 5,177,901 A * | 1/1993 | Smith | B24B 1/00 125/11.01 |
| 5,371,975 A | 12/1994 | Lundmark | |
| 5,470,466 A * | 11/1995 | Schaaf | B01D 21/0009 209/223.2 |
| 5,547,414 A | 8/1996 | Ohmori | |
| 5,643,055 A | 7/1997 | Linzell | |
| 5,904,457 A | 5/1999 | Suwijn et al. | |
| 6,159,086 A * | 12/2000 | McClurkin | B24B 55/06 451/451 |
| 6,205,371 B1 | 3/2001 | Wolter-Doll | |
| 6,217,409 B1 | 4/2001 | Stadtfeld et al. | |
| 6,407,523 B1 | 6/2002 | Allan | |
| 6,566,871 B2 | 5/2003 | Holzl | |
| 6,577,917 B1 | 6/2003 | Ronneberger | |
| 6,832,606 B2 * | 12/2004 | Yamada | B28D 5/007 125/13.01 |
| 8,137,160 B2 | 3/2012 | Kurashiki et al. | |
| 2001/0017540 A1 | 8/2001 | Arai | |
| 2003/0129927 A1* | 7/2003 | Lee | B23H 3/00 451/41 |
| 2004/0132393 A1* | 7/2004 | Reich | B24B 23/00 451/456 |
| 2008/0051006 A1* | 2/2008 | Yamada | B24B 49/04 451/1 |
| 2009/0156097 A1* | 6/2009 | Pilkington | B24B 7/00 451/5 |
| 2010/0120337 A1* | 5/2010 | Kuriyama | B23B 1/00 451/61 |

OTHER PUBLICATIONS

Aguiar, Paulo R. et al.; "In-Process Grinding Monitoring by Acoustic Emission"; IEEE; Pub. 2004 ("the Aguiar publication").

Liu, Qiang et al.; "Investigation of Acoustic Emission Signals under a Simulative Environment of Grinding Burn"; www.sciencedirect.com; Pub. 2005 ("the Liu publication").

Badger, Dr. Jeffrey; "Grinding: A Pictoral Odyssey; An Examination of the Grinding Process, et al."; Cutting Tool Engineering Magazine, Feb. 2009, vol. 61, Issue 2 ("the Badger Pub").

Dabade, Uday A. et al.; "Analysis of Chip Formation Mechanism in Machining of Al/SiCp Metal Matrix"; www.sciencedirect.com; Pub. 2008 ("the Dabade publication").

Jawahir, I.S.; "The Chip Control Factor in Mechinability Assessments: Recent Trends"; www.sciencedirect.com; Pub. 1988 ("the Jawahir publication").

Sutter, G.; "Chip Geometries during High-Speed Machining for Orthogonall Cutting Conditions"; www.sciencedirect.com; Pub. 2005 ("the Sutter publication").

Wojtas, A.S. et al.; "Detection of Thermal Damage in Steel Components after griding Using the Magnetic Barkhausen Noise Method"; ENCDT; www.ndt.net.com; Sep. 1998m vol. 3, No. 9.

Rogelio L. Hecker, Steven Y. Liang, Xian Jian Wu, Pin Xia, David Guo, Wei Jin; "Grinding force and power modellng based on chip thickness analysis"; Int J Adv Manuf Technol (2007) 33: 449-459 DOI 10.1007/s00170-006-0473-y; Published online: Apr. 11, 2006; © Springer-Verlag London Limited 2006.

* cited by examiner

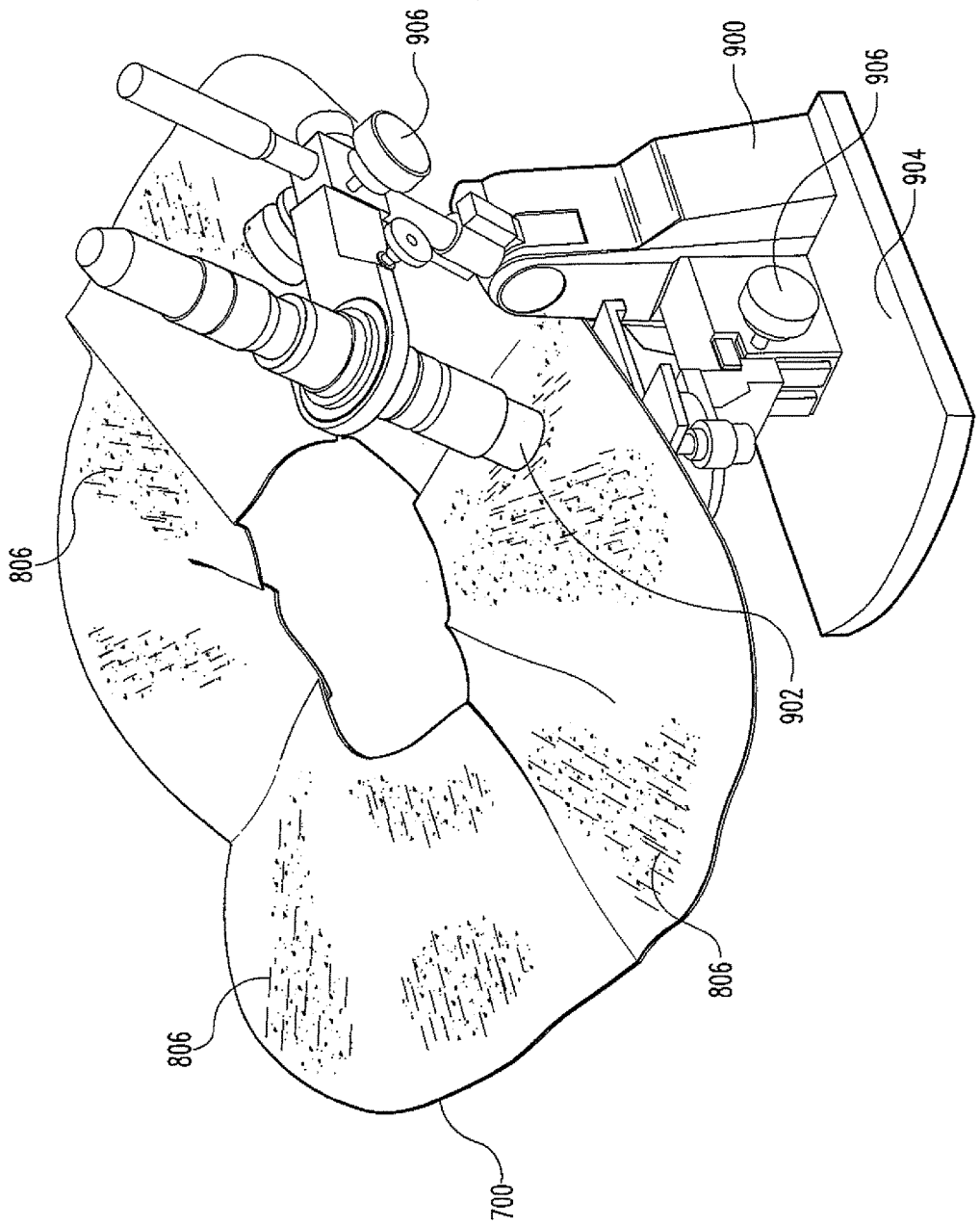

METHOD FOR DETECTING AND/OR PREVENTING GRIND BURN

RELATED APPLICATIONS

This application is a divisional application of U.S. patent application Ser. No. 13/958,814, filed Aug. 5, 2013, which is a divisional application of U.S. patent application Ser. No. 13/617,804, filed Sep. 14, 2012, which is a divisional application of U.S. Pat. No. 8,353,739, filed Dec. 8, 2009 entitled "Method for Detecting and/or Preventing Grind Burn," the disclosures of which are expressly incorporated herein by reference in their entirety.

BACKGROUND

The present disclosure relates to a grinding operation, and in particular, to a method of detecting and/or preventing grind burn on a workpiece being ground.

The design and manufacture of bearings, gears, shafts and many other surface hardened components in modern automotive and aerospace industries pose significant challenges. These components require special attention in choosing the correct parameters for heat treatment as well as for subsequent machining processes. The latter, if carried out inaccurately, may reduce the surface hardness and diminish the compressive surface stresses after surface hardening. Accurate and continuous control of machining processes such as grinding is essential in today's production of these components.

Grinding is a machining process used in the manufacture of high accuracy components to achieve the required tolerance. Compared with other machining processes, grinding requires a very large energy input per unit volume of material removed. The majority of this energy is converted to heat, which is concentrated in the surface layers of the material, within the grinding zone. As such, a sharp increase in the localized temperature within the surface can occur. Gears and other components that are hardened and subsequently ground can be subjected to surface tempering of these localized areas known as "grind burns." The severity of the damage, i.e., grind burn, will depend on the temperature the workpiece surface attained when ground. In a gear, for example, a grind burn can lower the surface hardness, lower the contact fatigue life of the gear, and cause microcracks in a burnt tooth, which negatively affects the fatigue life of the gear.

There are several factors that contribute to the generation of grind burns. Such factors can include 1) a high stock removal rate during grinding; 2) unexpected increase in stock removal from a tooth surface due to nonuniform heat treat distortion; 3) high grinding wheel hardness; 4) imbalance of grinding wheel; 5) infrequent dressing of the grinding wheel; and 6) insufficient coolant for removing generated heat. In a conventional process control method, grind burns are detected after the grinding operation. There are two primary conventional methods for inspecting a gear, for example, for grind burns: 1) a destructive method based on microhardness reading of the surface below the burnt area; and 2) a non-destructive method such as nital etching. The destructive method for inspecting gears requires the gear to be destroyed and therefore renders it unusable. This method is clearly disadvantageous because not all gears can be tested, and the gears which are not tested may suffer damage that is not detectable.

On the other hand, nital etching is currently considered the industry standard for inspecting gears for grind burns. Nital etching comprises the following steps: 1) cleaning the gear and then dipping the gear in nitric acid with 3%-5% alcohol or water; 2) rinsing the gear with water; 3) dipping the gear in alcohol; 4) bleaching the gear with hydrochloric acid in 4%-6% alcohol or water; 5) rinsing the gear again with water; 6) neutralizing the gear with an alkali solution (minimum pH of 10); 7) rinsing the gear a third time with water; 8) dipping the gear in alcohol; and 9) applying an oil with rust preventative to the gear. After the etching procedure, the gear is visually inspected for evidence of grind burns under a light source of 200 footcandles (ftc) minimum. A gear that has a grind burn can have a dark gray, blue, or black appearance, whereas a gear that is free of grind burns can have a light gray or light brown appearance. A limited amount of grind burn on a gear tooth may be acceptable, but only if the tooth is part of a non-fracture-critical gear or if the grind burn does not extend into a critical area of the tooth.

There are several disadvantages to nital etching. First, nital etching can reduce the size of the gear. For example, approximately 0.003 min of material can be removed from the gear each time the etching process is performed. Any portion of the gear that requires a tight tolerance which should not be exposed to nital etching must be masked to avoid stock removal (which requires an additional step in the nital etching process described above). A second disadvantage with nital etching is the resulting appearance of the gear. There may be areas of discoloration on the gear as a result of nital etching. Processes for removing the discoloration may cause stock removal or surface texture changes. Another disadvantage with nital etching is corrosion of the gear. While it is possible to add corrosion protection to the gear, this requires an additional step to the above-described nital etching process. A fourth disadvantage is hydrogen embrittlement when atomic hydrogen enters the hardened steel or other alloys. Hydrogen embrittlement may cause a loss in ductility, load-carrying ability, and/or cracking. Catastrophic brittle failures are also possible. Other disadvantages with nital etching include environmental considerations, safety concerns, increased costs, and lead time. Also, the quality of the inspection of a gear or part after nital etching depends on the visual capability, skill, and awareness of the inspector performing the inspection.

In addition, not all manufactured parts are required to be inspected for grind burns using the nital etching process. According to industry standard ANSI/AGMA 2007-C00, which specifies standard procedures and requirements for the detection and classification of localized overheating on ground surfaces by chemical etch methods, there is no "specific acceptance or rejection criteria" contained therein for inspecting ground parts. In some instances therefore only a certain percentage or quantity of parts made are inspected. As such, a percentage of parts being made are never tested for grind burns.

Other non-destructive methods for detecting grind burns include Magnetic Barkhausen Noise (MBN) and X-ray diffraction. MBN measures residual stress in the gear, but this method has difficulty identifying "good quality" gears from "poor quality" gears. On the other hand, the X-ray diffraction method is expensive and time-consuming. Another detection method is to shot peen the surface of the gear. If the surface is soft, the method detects this softness due to the texture of the gear. The test is subjective, however, and relies on visual inspection for identifying grind burns.

What is needed therefore is an improved method of detecting and preventing grind burns on a ground workpiece which overcomes the disadvantages of the prior art and which can be implemented for testing all ground components being made.

SUMMARY OF THE DISCLOSURE

The present disclosure provides a method for detecting and/or preventing grind burns on a ground workpiece such as a gear. In an exemplary embodiment, the method determines whether a grinding wheel is properly dressed before a grinding operation. The method includes placing a probe in contact with the grinding wheel and measuring with the probe an induced signal in the grinding wheel. The measured induced signal is compared to a threshold, and if the measured induced signal is greater than the threshold, it is inferred that the grinding wheel needs to be dressed or replaced. Moreover, if the measured induced signal exceeds the threshold, a presence of material buildup is detected on the grinding wheel. As the probe is placed in contact with the grinding wheel, the probe induces an electric field in the grinding wheel. As the electric field is induced, the probe detects the induced signal in the grinding wheel.

In a different embodiment, a method is provided for detecting grind burn during a grinding operation. The method includes removing material from an object during the grinding operation. The material that is removed from the object is collected and inspected for an indication of grind burn. Filter paper, for example, can be positioned substantially beneath the object for collecting the material, or alternatively, a magnet or other similar device can collect the material. As material is collected on the filter paper, a correlation can be made between the location of the material collected on the filter paper to the location on the object from which the material is removed. The collected material can be inspected by an instrument at at least 173× magnification or greater. The instrument can be a camera, microscope, or other similar device. Indications of grind burn can include discoloration or a change in thickness of the collected material. If there is discoloration or a change in thickness of the collected material, grind burn may be detected on the object.

In another embodiment, a method is provided for detecting and/or preventing grind burn on a gear. The method includes grinding the gear with a grinding wheel during a grinding operation. During the grinding operation, an acoustic emission signal produced by the grinding is measured with a sensor. An electric field is induced in the grinding wheel and unwanted conditions that cause grind burn are detected. In one form of the method, a probe can be placed in contact with the grinding wheel thereby inducing a signal therein. The probe can measure the induced signal and compare the induced signal to a threshold. If the measured induced signal exceeds the threshold, it can be concluded that the grinding wheel has material buildup from the gear and the grinding wheel needs to be dressed or replaced.

In another form of the method, the acoustic emission signal is compared to a threshold, and if the measured signal exceeds the threshold, a determination is made that too much material is removed from the gear. Moreover, grind burn can be detected if the measured acoustic emission signal is greater than the threshold. In addition, if the measured acoustic emission signal is greater than the threshold, a preventative measure can be implemented by suspending the grinding operation.

In a different form of the method, swarf which is removed from the gear during the grinding operation is collected. The swarf can be collected by filter paper, for example, which is positioned substantially below the gear. The collected swarf can be inspected for an indicia of grind burn such as discoloration or a change in thickness of the collected swarf. If discoloration or a change in thickness is inspected, grind burn is detected on the gear.

In an alternative embodiment, a large-scale production method is provided for making gears. The method includes establishing tolerances for the amount of material removed from stock to form the gears. A grinding wheel is selected that maximizes cutting efficiency and requires infrequent dressing. Also, the number of passes the grinding wheel will make for removing material from the stock is determined. The method also includes establishing a threshold amount of coolant flow to be dispensed to the grinding wheel and stock during the grinding operation. The stock is ground by the grinding wheel during the grinding operation and gears are made from the stock. A condition favorable for generating grind burn on the gears is determined before, during, and after the grinding operation. If such a condition is determined, one or more parameters of the grinding operation is adjusted to eliminate the condition and the steps of grinding the stock with the grinding wheel, making gears, and determining a condition favorable for generating grind burn are repeated.

An advantage of the inventive method is that grind burns can be detected and prevented before, during, and after the grinding operation. During the grinding operation, for example, the acoustic emission generated is measured and compared to a threshold. If the measured acoustic emission is greater than the threshold, it is inferred that grind burn is likely being generated and the grinding operation can be suspended for further evaluation. Likewise, after the grinding operation, swarf collected during the grinding operation is inspected for indicia of grind burn. Therefore, even if the acoustic emission generated during the grinding operation does not detect grind burn, analyzing the collected swarf afterwards may suggest otherwise. As such, the inventive method includes safety nets for detecting grind burns.

The inventive method also includes a process for monitoring the condition of the grinding wheel. As will be described below, studies show that almost 15% of the damage suffered by a gear during a grinding operation is due to an improperly dressed grinding wheel. Thus, the present disclosure provides a method that detects material buildup on the grinding wheel that, if not properly removed before a subsequent grinding operation, can lead to grind burn on a gear or other object being ground.

Another advantage of the inventive method is that every manufactured gear is tested for grind burn. More importantly, the grinding of each gear tooth is monitored for grind burn during the grinding operation. This allows immediate detection of grind burn and does not rely solely on visual inspection. Moreover, the inventive method can be implemented using tooling and resources available in the same manufacturing facility in which a gear or other ground workpiece is made. This can provide cost savings and test results much sooner than conventional detection processes which in some instances require finished parts to be shipped to an off-site test facility for testing.

BRIEF DESCRIPTION OF THE DRAWINGS

The above-mentioned aspects of the present disclosure and the manner of obtaining them will become more apparent and the disclosure itself will be better understood by reference to the following description of the embodiments of the disclosure, taken in conjunction with the accompanying drawings, wherein:

FIG. 9 is a perspective view of swarf collected during a grinding operation being inspected by a camera.

Corresponding reference numerals are used to indicate corresponding parts throughout the several views.

DETAILED DESCRIPTION

The embodiments of the present disclosure described below are not intended to be exhaustive or to limit the disclosure to the precise forms disclosed in the following detailed description. Rather, the embodiments are chosen and described so that others skilled in the art may appreciate and understand the principles and practices of the present disclosure.

The present disclosure relates to a process control method of detecting and/or preventing grinding burns on a ground workpiece during and after a grinding operation. One of the purposes behind process control methods is to control the output of a specific process. In the case of manufacturing gears, for example, the process control method or system is designed to establish parameters for each step in the manufacturing process to ensure the manufactured gears are made substantially the same.

Figure 1:
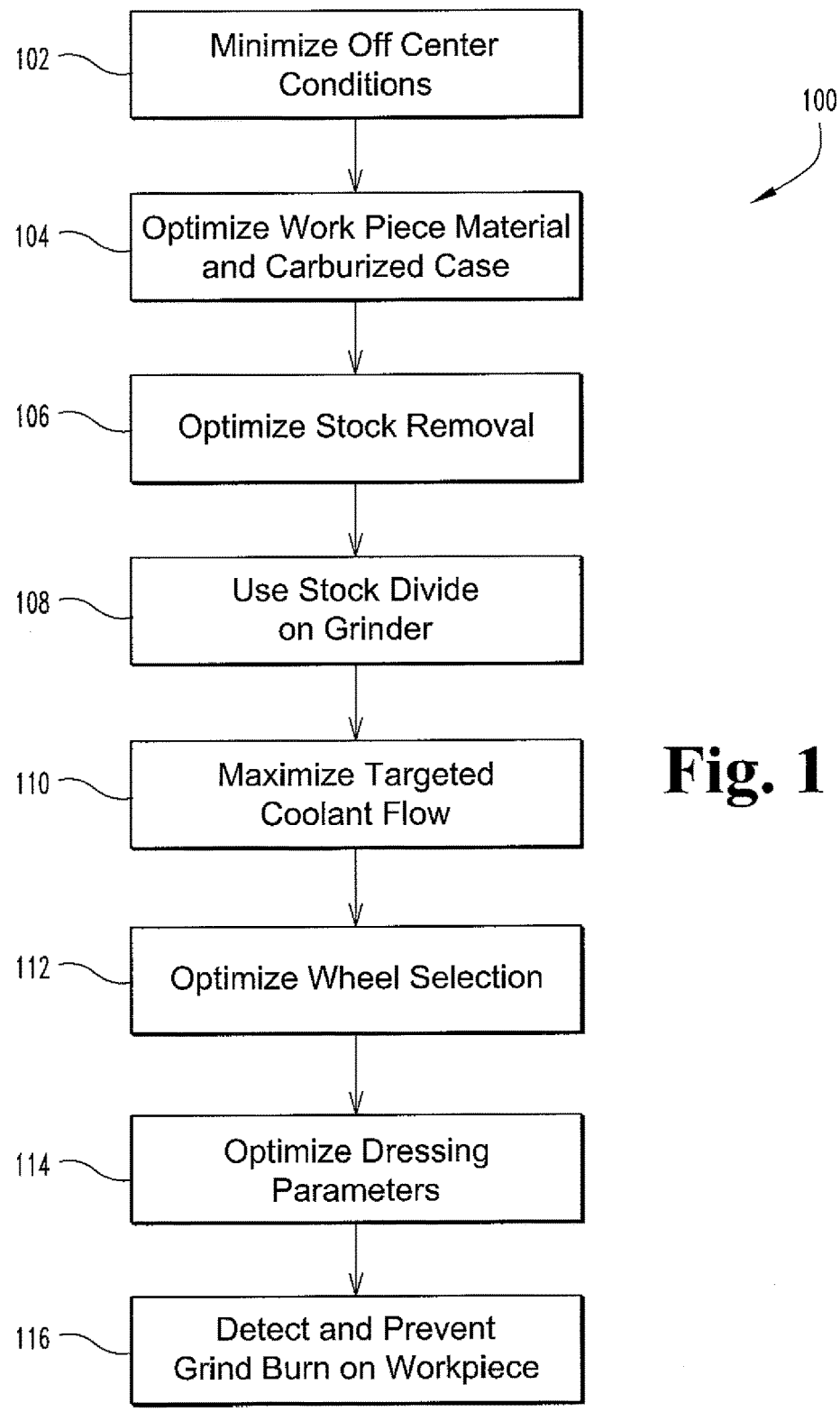
FIG. 1 is a flowchart of an embodiment of a process control system for manufacturing a gear.

With reference to FIG. 1, an exemplary embodiment of a process control method is provided. While other process control methods may include additional or fewer steps for manufacturing a gear, the embodiment of FIG. 1 provides a method 100 of eight parameters or conditions which can affect the quality of a ground workpiece. In block 102, the method 100 seeks to minimize off center conditions or runout. The pitch diameter of a gear, for example, can be 3 inches from tooth-to-tooth. However, there can also be localized areas where the diameter is slightly smaller or larger (e.g., 2.995" or 3.005"). In these circumstances, the gear has runout of 0.005" from the centerline of the gear. If the diameter exceeds a runout threshold, there can be unbalanced stock removal during a grinding operation. To reduce or minimize runout, machines, tools, and gages used for machining the workpiece must meet certain specifications. In addition, the quality of the tooling used for holding the workpiece, the setup, and repair of the machines and tooling are routinely checked for runout problems.

In block 104, the process control method further includes ensuring and maintaining the quality of the workpiece material. The quality and preparation of the workpiece material can influence the results of dimensional changes in the workpiece after carburizing and hardening processes, and most importantly, the susceptibility of the workpiece to surface tempering during gear grinding, for example. Quality refers to the workpiece, and in particular, to its chemistry, grain structure, microstructure, reduction ratio, and the like. In a process in which a gear is manufactured, the quality can refer to the material, e.g., steel, as well as dimensional tolerances being held before heat treat. Conventionally used carburized steel grades for gears include SAE 8620, 4320, and 9310. The grade refers to the chemical composition of the material including carbon, manganese, nickel, chromium, molybdenum, etc.

In addition, the process for making the steel can have significant effects on the service life of the gear and heat treat response of the material. For example, a regular grade of steel (e.g., SAE 8620) with no special processing and a bearing quality/aircraft quality grade which is vacuum degassed while the metal is still molten to remove nonmetallic inclusions from the metal. Additionally, there are strand cast and ingot cast processes which can yield different properties. After the metal is cast and rolled into usable product shapes, the final thermal process makes a significant difference in the dimensional response when it is carburized as a gear.

Gears can be "core treated" before carburizing in an attempt to achieve a stress-free state and minimize any dimensional change during the carburizing process. This involves making a gear blank that has some extra stock on it, but without any gear teeth formed therefrom. The gear blank can be heated, quenched in oil, and reheated to "temper" or soften the blank so that the final shape can be cut with gear teeth.

The carburizing process also relieves any residual stress in the workpiece material because carburizing involves heating the material to about 1700° F. As the workpiece is heated, any stresses in the workpiece cause localized portions to change shape as the stress is relieved. This is a major source of dimensional change. Therefore, it is most desirable to have a stress-free workpiece before carburizing.

There are also quality concerns related to the machining quality prior to heat treat. Some gears, especially large gears that have at least an 8 inch outer diameter, are restored to a usable dimensional state by a process called "press quenching." The other and more common process is called "free quenching" or simply quenching in oil. Press quenching involves heating the part to about 1550° F. and then moving it to a press with special fixtures that clamp the part flat while it is still red hot and then dispenses oil over the part until it is immersed in oil. This process can only restore the part to a flat condition on the gear face and reset the axial dimension to a pre-heat treat state.

In the carburizing process, parts can droop, distort, bend, "potato chip", etc., because the steel is soft at higher temperatures and sags. This becomes a real problem especially on larger gears (e.g., gears having large outer diameters). In general, the critical dimensions for the part are those that contact the press and they must be held at ±0.001" prior to heat treat in order to obtain acceptable results after heat treat.

In block 106, another process control in method 100 is the optimization of stock removal. There are at least four ways this is achieved including 1) targeted size (bobbing), 2) range of growth (heat treat), 3) minimized distortion (heat treat), and 4) amount and number of passes on a grinder. As for targeted size, the targeted pitch diameter of the gear or workpiece establishes the amount of stock to be removed by the gear grinder. Not only should the target avoid removing more stock than necessary, but also the applied tolerances should support reducing variation in stock removal from tooth to tooth, piece to piece, and operation to operation.

The growth, or range of growth, of the workpiece through carburizing and hardening can result in excess stock being removed per flank. In some cases, however, there may not be enough stock removed to form a "good" quality gear if the workpiece does not grow as expected. In general, a gear that has a diameter of 4 inches may not change. A gear having a diameter less than 4 inches will likely shrink, whereas a gear having a diameter greater than 4 inches will likely grow. For example, a gear may grow from about 0.001-0.0015 inches per inch of diameter depending on the SAE grade for larger gears through the carburizing process. To ensure proper growth, workpiece material is specified at the time of purchase and the machining process is usually CNC controlled. The growth or shrinkage resulting from the heat treat process is identified and compensated for during the grinding process. As an example, if a gear has a finished diameter of 12.0000 inches, the expectation would be for the gear to grow about 0.012 inches as a result of the heat treat carburize process. When the gear teeth are hobbed, the growth of the gear is compensated for by cutting the pitch diameter at about 11.9940 inches. After heat treat, the gear would be 12.0060 inches after growing by 0.012 inches. The gear is then ground to 12.0000 inches on the grinder.

The workpiece or gear can be subject to distortion through carburizing and hardening. As such, the process control method 100 takes into account distortion, which can be referred to as taper, crown, hollow, or profile variation of the workpiece. Failure to take distortion into account can cause excess stock removal per flank when the workpiece is ground. As an example, assume a gear having a final diameter of 12 inches is desired. When the gear is first machined, the pitch diameter may be 11.994 inches as cut and the outside diameter of the gear is concentric and cylindrical. Taper occurs when the pitch diameter at opposite ends of the gear tooth differ. In this example, following heat treat, one end of the gear may have a diameter of 12.006 inches and the other end is 12.001 inches. When grinding begins to cut the pitch diameter to 12.000 inches, the grinder contacts the end having the diameter of 12.006 inches first. Depending on the setup of the grinder, excess stock may be removed during the first pass which can cause the gear to suffer burns. This can be taken into account by measuring the workpiece or gear before the first grind pass. New equipment can access the stock condition and choose an appropriate course of action for grinding the gear to specification. In addition, distortion can be minimized by selecting heat treat variables that make the process more robust to variation.

Lastly, optimizing stock removal includes determining the number of passes a grinder will make on a workpiece and how much stock is removed during each pass. The purpose of this step is to determine the amount of stock to be removed during a pass and the number of passes which economically grinds the workpiece without "loading" the grinding wheel or having the grinding wheel "rub" the workpiece excessively thereby creating undue friction and/or heat in the work zone. Once the amount of stock removal and number of passes is determined, these quantities are provided to the CNC gear grinder.

The process control method 100 of FIG. 1 includes block 108 which applies stock divide technology on each workpiece prior to grinding. This technology minimizes the risk of unequal stock removal during the 360° rotation of the workpiece. On a CNC grinder, for example, the grinding wheel makes contact with a predefined number of spaces between gear teeth. Calculations are made by the grinder to determine the centerline of a tooth space, thereby balancing stock removal from side-to-side.

In block 110, the amount of coolant flow directed into the "work zone" during the grinding operation is determined. The "work zone" is defined as the location or area in which the grinding wheel contacts and removes material from a workpiece. Coolant is important to removing heat between the grinding wheel and the workpiece during the grinding operation. When the maximum amount of coolant flow is directed into the "work zone," the risk of surface tempering is reduced. Different types of coolant can be used such as, for example, oil, synthetic, or water based. During a conventional grinding cycle, between approximately 90-120 psi of coolant is dispensed into the "work zone." The pressure can be different for other grinding cycles. To support this amount of coolant pressure, the coolant system can have a 500 gallon capacity with temperature controls and a filtering system.

The selection of the grinding wheel in block 112 of the process control method 100 is another important consideration when manufacturing a quality part. Hardness and grain size are two criteria used for specifying grinding wheels. Other specifications for selecting grinding wheels include abrasive type, abrasive size, grade or hardness, structure, and bond. The purpose or goal is to correlate the resultant wheel breakdown to the wheel dressing parameters and required cycle time. In other words, the purpose of the grinding operation is to remove material from the workpiece with abrasive action for achieving tight tolerances and fine surface finishes. The grain structure of the grinding wheel acts as a cutting tool for forming very small chips. Grinding wheels are self-sharpening tools due to the friability of the bond between grains. Friability is the ability to fracture under pressure so that as the cutting edges become dull, the grain breaks off and exposes new, sharp cutting edges. However, the self-sharpening phenomenon is supplemented with regular wheel dressing for quality assurance. As one skilled in the art understands, grinding wheels must be dressed periodically after grinding a workpiece so that material from the workpiece can be removed from the grinding wheel and the uniformity across the surface of the grinding wheel can be maintained.

Another consideration in the process control method 100 is the optimization of wheel dressing parameters. In block 114, dressing parameters include the frequency of dressing, the amount, and the rate at which the wheel is cleaned, sharpened, and "made like new" for the next workpiece. Wheel dressings can occur at different frequencies. For example, as a larger workpiece is being ground, the program can pause so that the grinding wheel can be dressed. In other instances, several parts can be ground before the wheel is dressed. During a dressing, any amount of material can be removed from the grinding wheel. As a non-limiting example only, about 0.002-0.005 inches of material can be removed from the grinding wheel. The rate at which the grinding wheel is dressed refers to the speed and feed used when dressing the wheel. A new grinding wheel can be any size depending on the type of application it is being used for.

As another non-limiting example, a new grinding wheel may have a diameter of 14 inches. The same grinding wheel may still be fully functional in the range of 10-11 inches in diameter. After the grinding wheel is dressed below a certain diameter, however, the grinding wheel must be replaced with a new one.

In block 116, the process control method 100 also includes the detection and/or prevention of grind burn on a workpiece. The effects of grind burn have been described above. In conventional process control methods, nital etching has been the industry standard for detecting grind burns. However, as described above, there are limitations and disadvantages associated with nital etching. As such, the present disclosure provides an alternative to nital etching that overcomes the limitations and disadvantages thereof.

Figure 2:
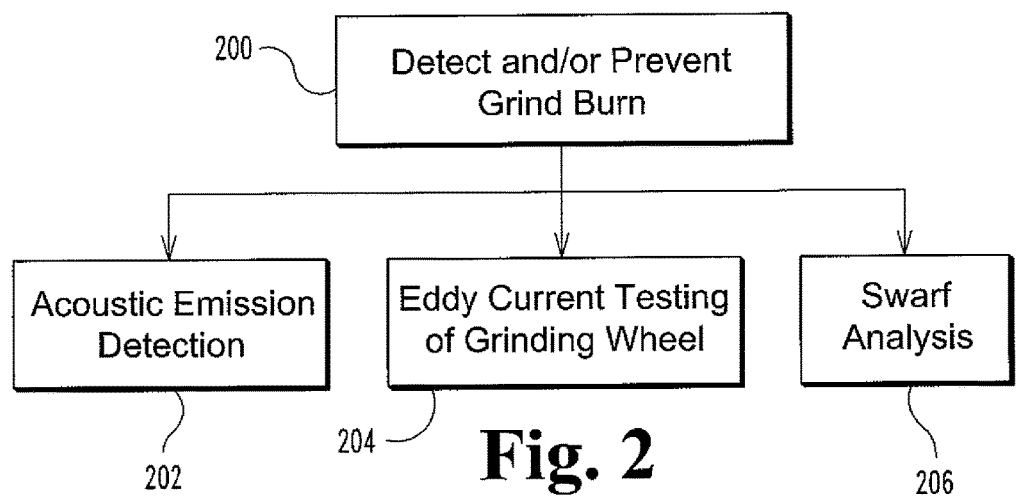
FIG. 2 is a flowchart of an embodiment for detecting and/or preventing grind burn.

With reference to FIG. 2, a method of detecting and/or preventing grind burn is provided. The method 200 includes acoustic emission detection 202, eddy current testing of the grinding wheel 204, and swarf analysis 206. Each of these methods can be performed individually or in combination with one another. In one embodiment, for example, method 200 may be performed by acoustic emission detection only. In a different embodiment, however, both acoustic emission detection 202 and swarf analysis 206 are performed. In another embodiment, all three detection/prevention methods can be carried out. As will be described in further detail, each method can detect and/or prevent grind burns on a workpiece by analyzing or testing a different component of the grinding cycle. As such, each method is independent of the others, but a complete analysis considers all three methods.

Figure 2A:
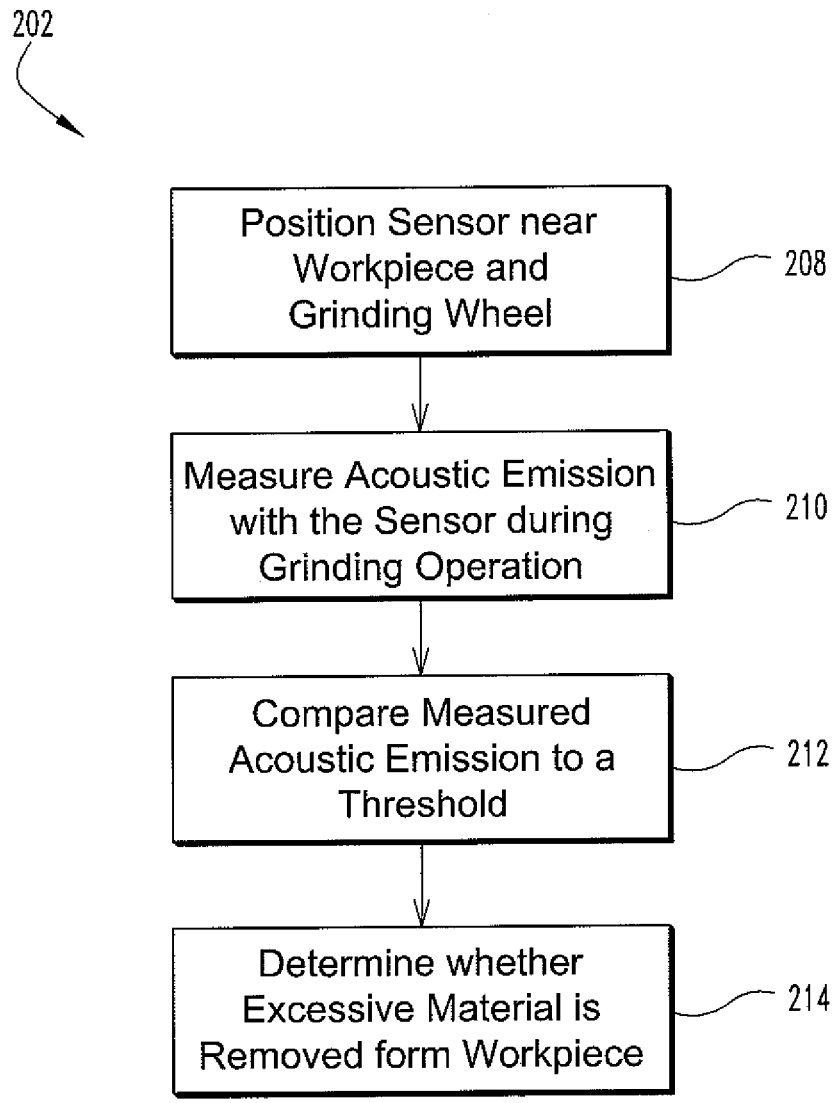
FIG. 2A is a flowchart of an embodiment for acoustic emission detection.
Figure 3:
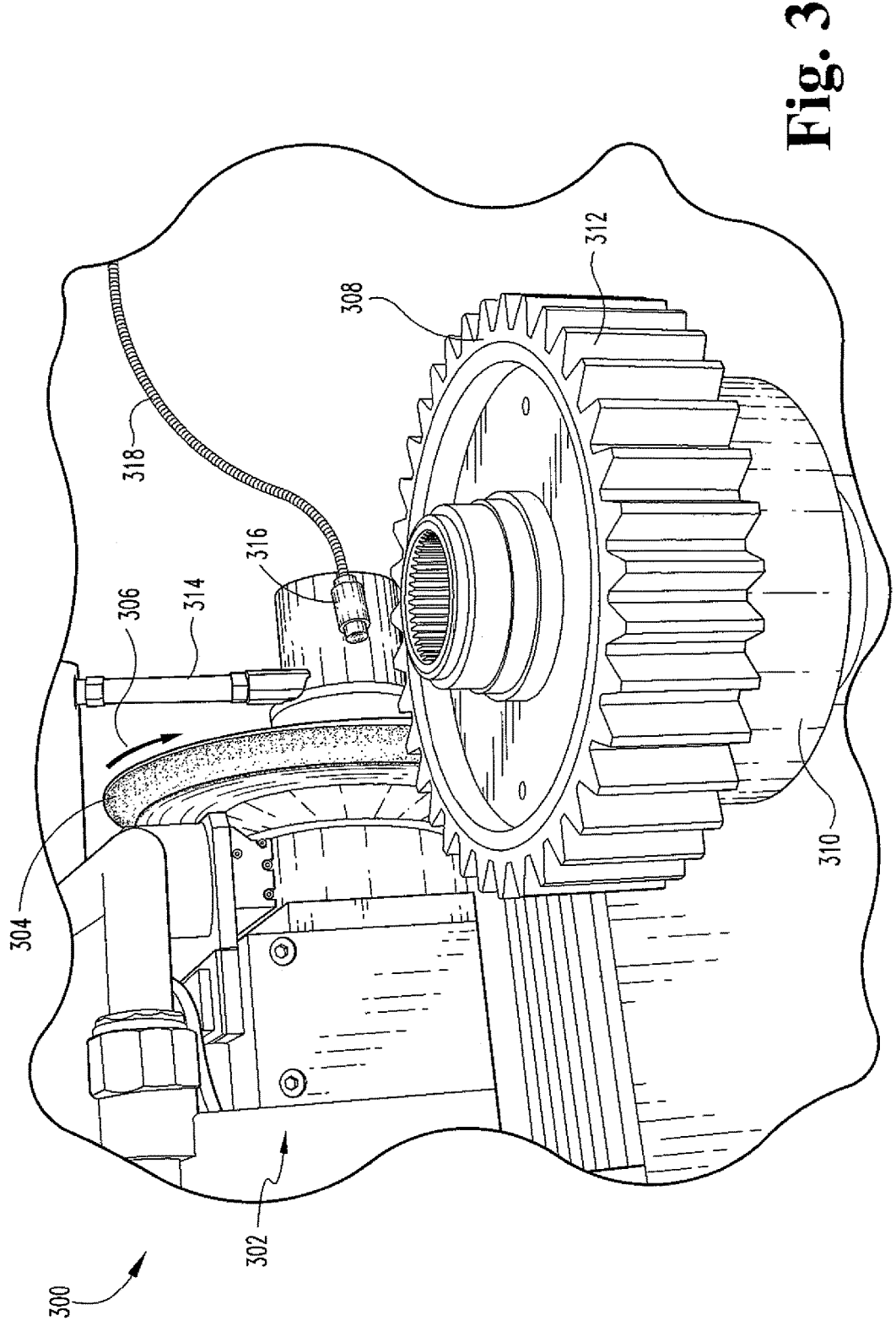
FIG. 3 is a perspective view of an embodiment in which a gear is undergoing an acoustic emission testing procedure.
Figure 4:
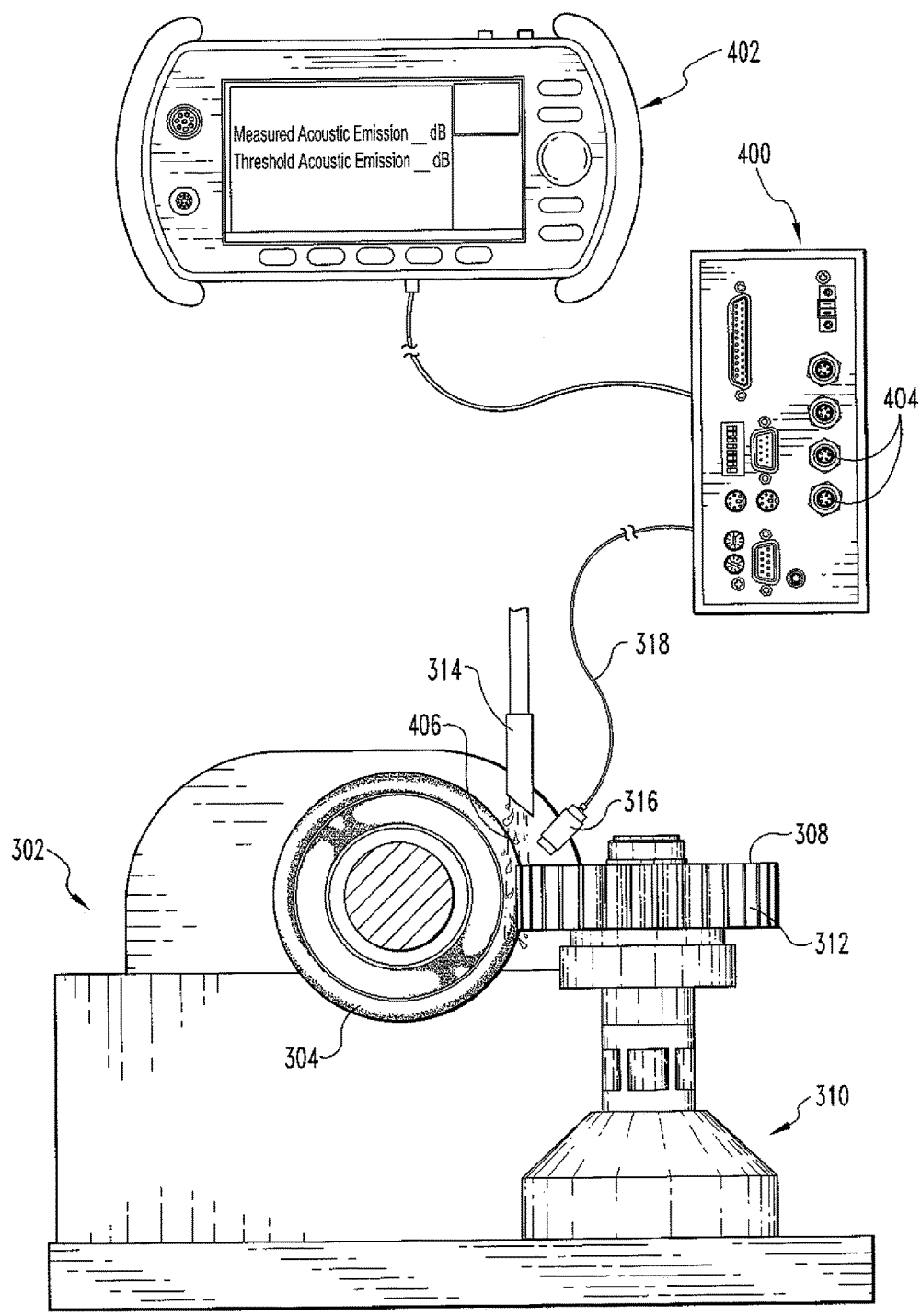
FIG. 4 is a schematic view of the acoustic emission testing setup of FIG. 3.

With reference to FIGS. 2A, 3, and 4, an exemplary embodiment is provided for detecting and/or preventing grind burns on a ground workpiece via an acoustic emission process 202. For illustrative purposes only, an exemplary setup 300 (FIG. 3) is shown of a gear 308 during a grinding cycle in which a grinding wheel 304 cuts material from the gear 308 to form the profile of a gear tooth 312. The acoustic emission process 202, however, is not limited to grinding gears. The process can also be used on other workpieces that are ground and subject to grind burns.

The grinding cycle can occur in a test facility 300 in which a grinder or grinding machine 302 includes a motor or the like for driving the grinding wheel 304. Depending on the size of the workpiece, the grinding wheel can be any size. For example, gear teeth for any type of gear including steering gears, range gears, power take-off (PTO) gears, etc. for assembling in a transmission can be formed using the grinding wheel. In FIGS. 3 and 4, the grinding wheel is about 14" in diameter. The grinding wheel can also be made of any material suitable for grinding gears such as aluminum oxide, Cubic Boron Nitride, Silicon Carbide, and Synthetic Diamond. One skilled in the art will appreciate that grinding wheels can be made of other materials as well.

During a grinding cycle, the gear 308 is fixed or secured in place by a workpiece holder 310. The workpiece holder 310 is able to rotate 360° so that each tooth 312 can be ground by the grinding wheel 304. Moreover, the grinding wheel 304 rotates in a direction indicated by arrow 306 and removes material from the flank of the tooth 312. Due to the friction caused between the gear tooth 312 and grinding wheel 304, a significant amount of heat is generated therebetween. To cool the gear tooth 312 being ground, a coolant dispenser 314 directs coolant 406 (FIG. 4) onto the gear tooth 312 during the grinding cycle. As noted above, different types of coolant can be used including oil, synthetic, or water based.

The acoustic emission method 202 of detecting and preventing grind hums from forming on the ground gear is performed during the grinding cycle. Unlike conventional methods for detecting grind burns such as vital etching which can only detect grind burns after grinding, the acoustic emission method 202 allows for immediate detection of grind burns during the grinding cycle. As a result, the acoustic emission method 202 provides the opportunity to detect grind burns before they form on the gear tooth 312. To do so, an acoustic emission sensor 316 is positioned near the grinding wheel 304 and gear 308. In the illustrated setup 300 of FIGS. 3 and 4, the sensor 316 is spaced about 12 inches from the grinding wheel 304 and gear 308. The distance between the sensor 316 and "work zone," i.e., the area immediately surrounding the grinding wheel 304 and gear 308, can depend on the type of sensor being used. One non-limiting example of an acoustic emission sensor that can be used is made by Dittel, Auburn Hills, Mich. The acoustic emission sensor 316 is coupled to a processor 400 via a cable 318. The processor can include several connectors 404 that are adapted to receive cables, wires, and the like. Although only one acoustic emission sensor 316 is depicted in FIGS. 3 and 4, it is possible for a plurality of sensors to be implemented in the test setup 300. The processor 400 can receive data from the sensor 318 and results or computations can be displayed on a display monitor 402.

Before or during a grinding operation, the acoustic emission sensor 316 is positioned adjacent to the grinding wheel 304 and gear 308. The acoustic emission sensor 316 can be positioned automatically (e.g., a robot or automation system moves the sensor to different positions and orientations) or manually. For example, before a grinding operation, a test operator can position the sensor 316 in a desired location. Once the sensor 316 is in the desired position, the grinding wheel 304 begins rotating in the direction indicated by arrow 306. As this is done, a gear tooth 312 is brought into contact with the wheel 304 and material is removed from the tooth 312.

As material is removed from the gear during the grinding operation, an acoustic emission is produced between the interaction of the grinding wheel 304 and gear tooth 312. The emission consists of measurable frequencies primarily in the ultrasound range. As known by the skilled artisan, emissions that fall in the range of human hearing produce frequencies between about 16 Hz to 20 kHz. In the ultrasound range, frequencies are produced between 20 kHz and 1 GHz. Acoustic emissions can produce measurable frequencies between about 20 kHz and 2 MHz. The acoustic emission sensor 316 is able to detect the emissions during the grinding operation and communicate the measured emissions to the processor 400. The processor 400 can analyze the measured emissions and display the results on the display monitor 402.

An advantage of measuring the acoustic emission during the grinding cycle is that grind burns can be detected as the gear is being ground. It has been found that a certain level or threshold of acoustic emission is directly correlated with grind burns forming on a gear tooth. Moreover, when the acoustic emission remains below or does not exceed the threshold, grind burns do not normally form on the gear tooth being ground. As a result, the acoustic emission process 202 of FIG. 2 includes measuring the acoustic emission with the sensor 316 (block 210) and comparing the measured acoustic emission to a threshold (block 212). The measured acoustic emission can be displayed on the display monitor 402 along with the threshold acoustic emission.

In block 214, based on the results of block 212, a determination is made whether grind burns may be forming on the gear or workpiece. As described above, one way in which grind burns form is when too much material is removed from the gear or workpiece. When excessive material is removed from the gear or workpiece, the acoustic emission produced is greater than when a normal or desired amount of material is removed. An ancillary component of the acoustic emission process 202 is determining what level or value of acoustic emission equates to when a normal or desired amount of material is removed during the grinding operation. As a non-limiting example, when the desired amount of material is removed from the flank of the gear tooth 312, the sensor 316 may measure 10 dB of acoustic emission. Based on this "normal" or "targeted" acoustic emission, a threshold acoustic emission is determined such that once the measured acoustic emission is equal and/or greater than the threshold acoustic emission, a determination is made that conditions are favorable for grind burns to form. This real-time detection method is advantageous over nital etching and other conventional grind burn detection methods because each gear is being tested and results are immediately known. The machine operator can observe the display monitor 402 during the grinding operation and manually shut down the grinding machine 302. Alternatively, the system can be automated such that once the measured acoustic emission exceeds the threshold acoustic emission for a period of time the grinding operation is suspended. A warning system can also be provided that produces an audible and/or visual alert when the measured acoustic emission exceeds the threshold. The alert can be displayed on the display monitor 402, for example.

In this example, 10 dB refers only to the amplitude of the noise signal. Besides the amplitude, there may be a frequency shift or other sound measurement that can be made for identifying potential grind burns. In addition, one skilled in the art can appreciate other ways in which automated alarms and warning systems can be implemented for detecting and/or preventing grind burns forming on a workpiece.

As described above, the acoustic emission process 202 is a real-time test procedure for detecting and/or preventing grind burns from forming on a ground workpiece. A different embodiment for detecting and/or preventing grind burns from forming on a workpiece during a grinding operation is the eddy current testing process 204. Eddy current testing analyzes the grinding wheel subsequent to a grinding operation and determines whether the grinding wheel is properly dressed. Through various testing and studies, it has been determined that almost 15% of damage associated with the grinding of a workpiece is attributable to the dressing condition of the grinding wheel. As such, the eddy current testing process 204 provides another method for detecting and/or preventing grind burns from forming on a ground workpiece.

Figure 2B:
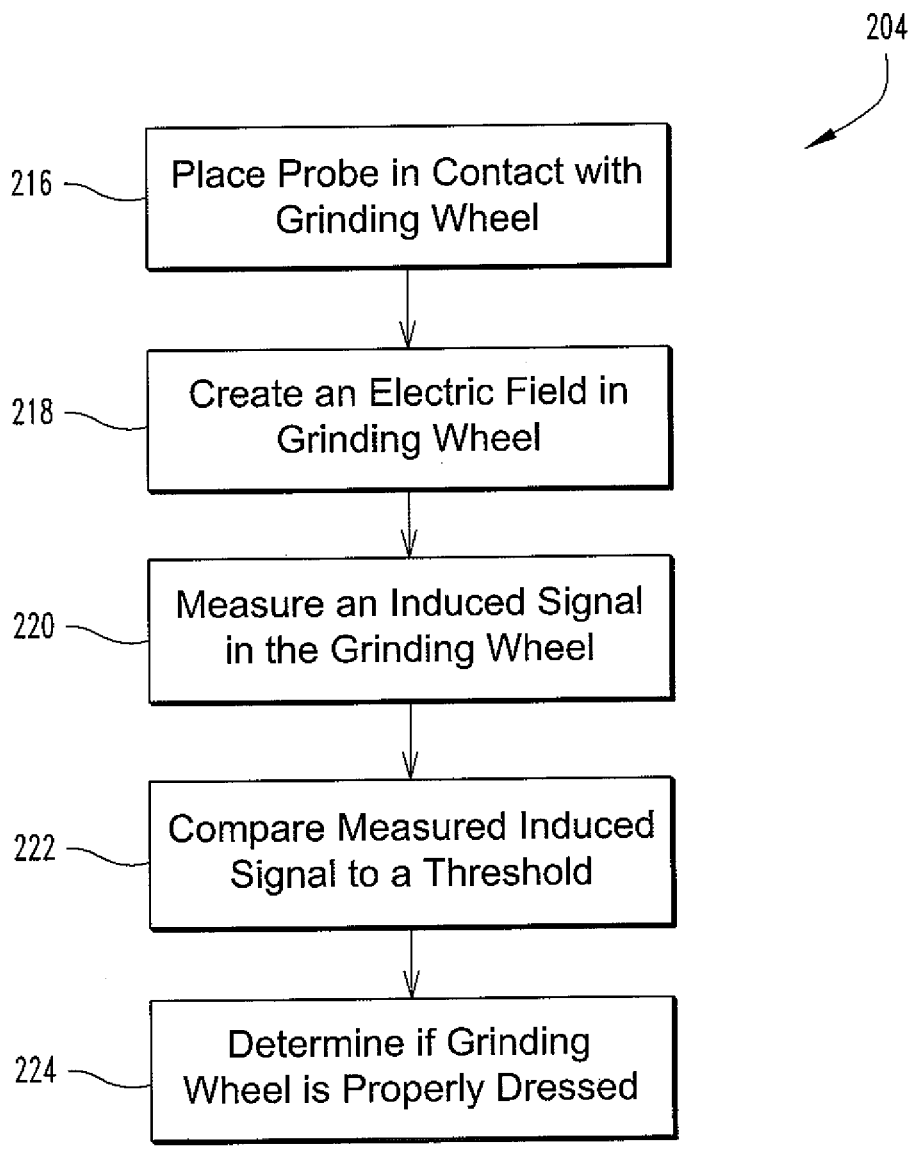
FIG. 2B is a flowchart of an embodiment for eddy current testing of a grinding wheel.
Figure 5:
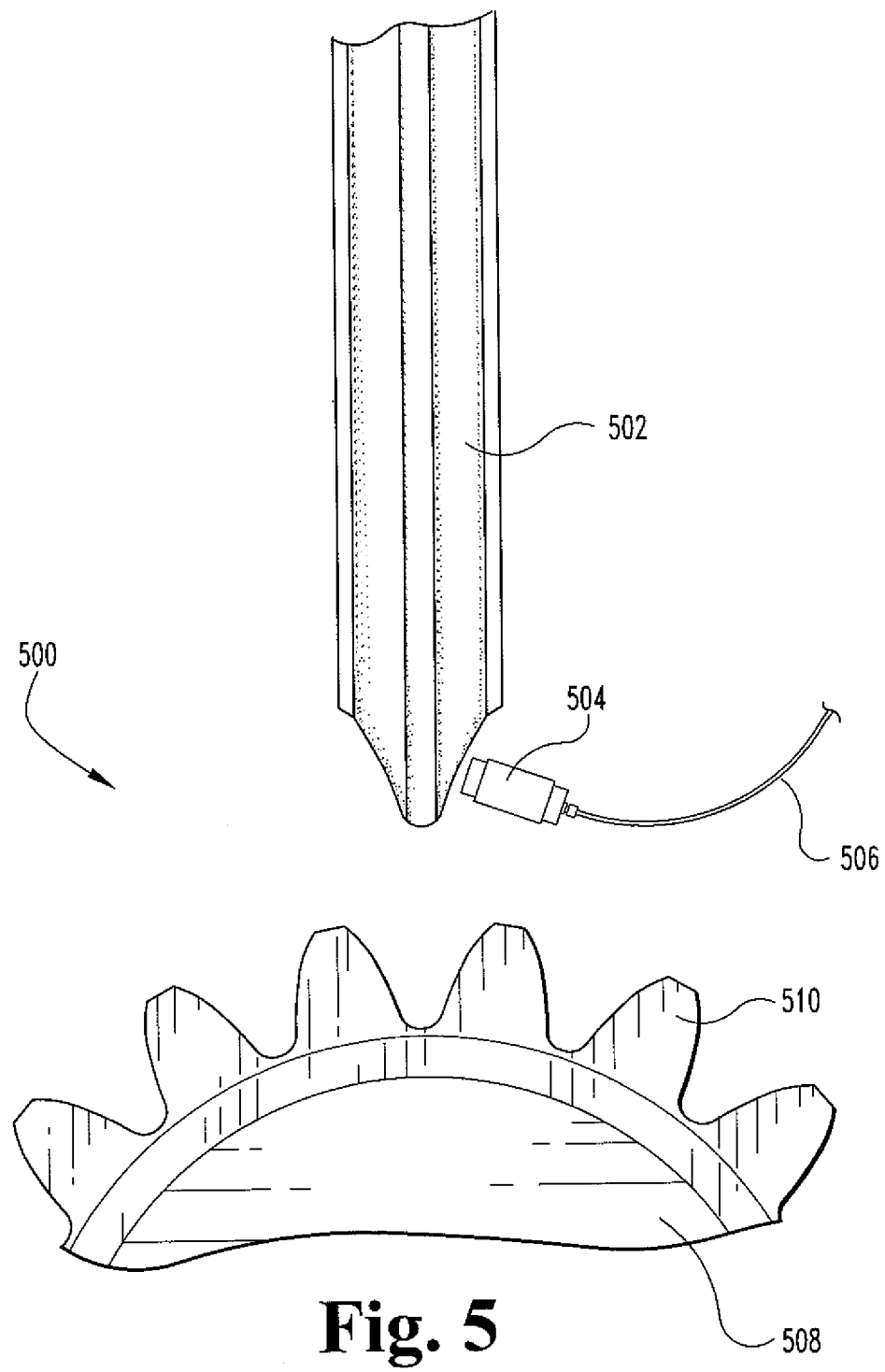
FIG. 5 is a top view of an embodiment of a grinding wheel undergoing eddy current testing.
Figure 6:
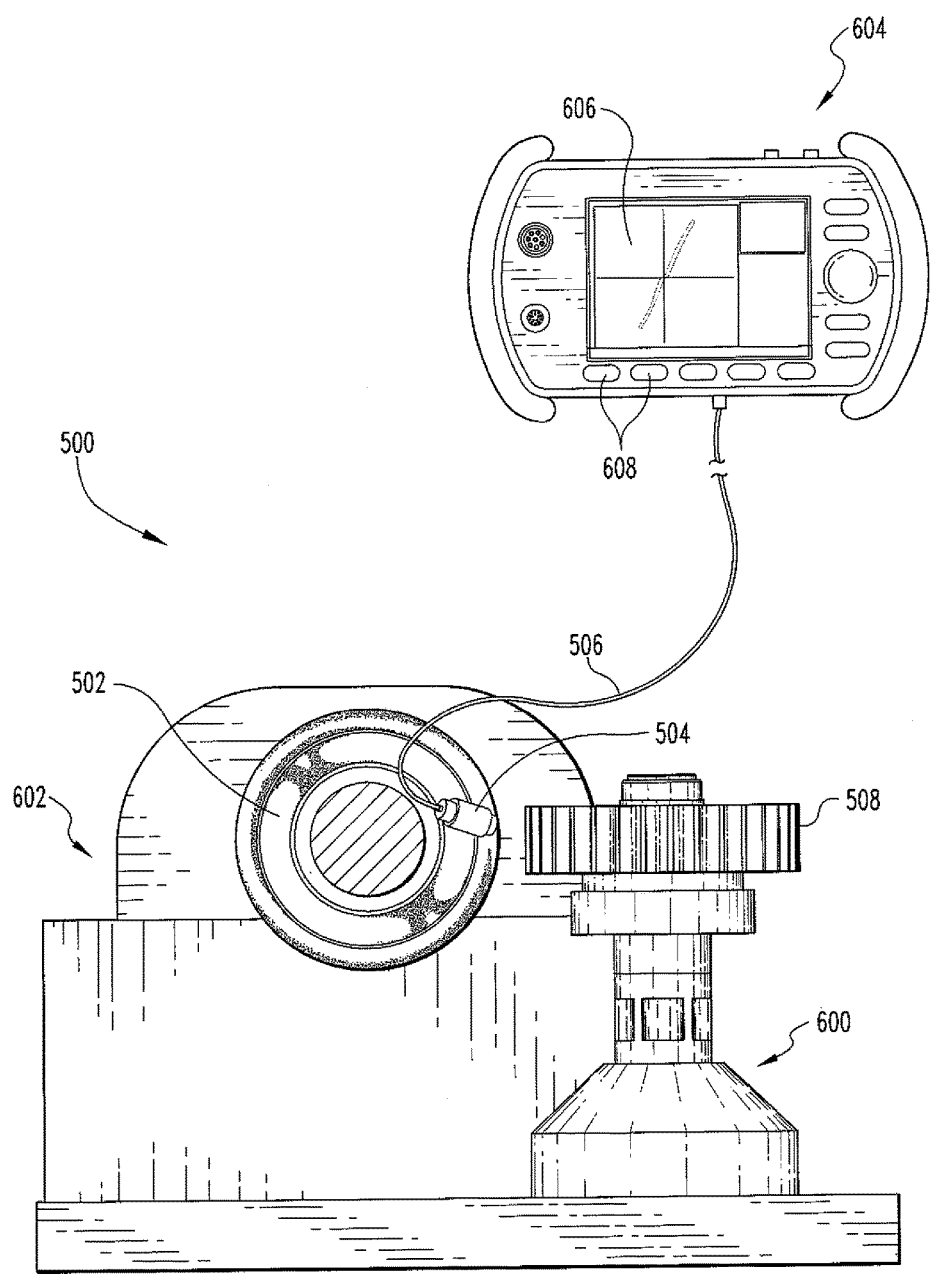
FIG. 6 is a schematic view of the eddy current testing setup of FIG. 5.

With respect to the illustrative embodiment of FIGS. 2B, 5, and 6, the eddy current testing process 204 is performed after a gear tooth 510 of a gear 508 is ground. In the setup 500 of FIGS. 5-6, the gear 508 is coupled to a workpiece holder 600. The workpiece holder 600 is positioned near a grinding machine 602, which includes a grinding wheel 502 powered by a motor or the like (not shown). The grinding wheel 502 can have any diameter and made of any material. As described above, one non-limiting example of a grinding wheel 502 has a diameter of about 14 inches and is made from aluminum oxide. The contour of the grinding wheel can also be either concave or convex depending on the shape of the gear tooth being formed.

After the grinding operation, the grinding wheel 502 is moved away from the gear 508 and, in block 216 of FIG. 2, an eddy current probe 504 is placed in contact with the grinding wheel 502. An example of an eddy current probe that can be used in this setup is a Statograph® 6.421 Probe available at Foerster Instruments, Incorporated, Pittsburgh, Pa. The probe 504 can be connected to a meter or scope 604 by a cable 506. The meter or scope 604 can have a graphical display 606 with user control buttons 608 for operating the meter or scope 604. An example of a meter or scope that can be used for eddy current testing can also be found at Foerster Instruments, Incorporated.

During the grinding operation, material that is removed from the workpiece can become embedded in the grains of the grinding wheel 502. In the case of a gear, which can comprise up to 98% iron, gear filings that are removed from the gear become embedded in the grinding wheel. If too much iron is embedded in the grinding wheel and the wheel is not dressed, further grinding with the same grinding wheel can generate grind burns on the gear tooth. In the case of an aluminum oxide grinding wheel, for example, the eddy current testing process 204 can detect a presence of iron embedded in the grinding wheel by creating an electric field in the grinding wheel (see block 218). In the eddy current sensor 504, there can be a primary and secondary coil (not shown). The primary coil can pass an electric signal such as current to the grinding wheel. As one skilled in the art understands, when an alternating current flows in a coil, the magnetic field of the coil can produce circulating eddy currents in close proximity to the conducting surface. In the present embodiment, if iron is embedded in the wheel, the electric field creates a reverse or induced signal in the grinding wheel. Iron is magnetic, and the induced eddy current has magnetic and resistive properties. As such, presence of iron is detectable via the magnetic component. In block 220, the secondary coil receives the induced signal and the probe 504 measures the strength of the signal. The measured signal can be displayed on the graphical display 606 in any form known to the skilled artisan (e.g., in graphical format, digital format, etc.).

In block 222, the measured signal is compared to a threshold eddy current value. The threshold can be established in a plurality of ways. One such way for determining the threshold is to perform the eddy current testing process 204 on a grinding wheel which has never been used. In such a case, there should be no induced eddy current signal and therefore the measured induced signal would measure 0 volts, for example. While it is possible for the measured signal to have different units such as dB, voltage is easy to measure and/or convert to from other units. In one aspect, if the threshold is 0 volts, any presence of iron embedded in the grinding wheel will create a measurement greater than the threshold. However, a small presence of iron embedded in the grains of the grinding wheel can be unavoidable and does not always result in grind burns. As such, in a different aspect, a threshold greater than 0 volts is established with the understanding that a greater presence of iron is allowed to be embedded in the grinding wheel. In one non-limiting example, any measured signal less than 0.25 mV is considered to be satisfactory for purposes of reusing the grinding wheel without dressing the wheel. This "determination" step comprises part of block 224 of FIG. 2.

In block 222, if the measured signal is greater than the threshold, this may not suggest that the gear has suffered surface tempering. Instead, it may indicate that continued use of the grinding wheel without dressing the wheel will provide favorable conditions for damaging the gear. Thus, if the grinding wheel needs to be dressed, about 0.002" of material is removed from the diameter of the grinding wheel and the wheel is ready for further grinding operations. The eddy current testing process 204 therefore provides an additional method of detecting and/or preventing grind burns from forming on a ground workpiece and ensuring that the grinding wheel is adequately dressed.

Figure 2C:
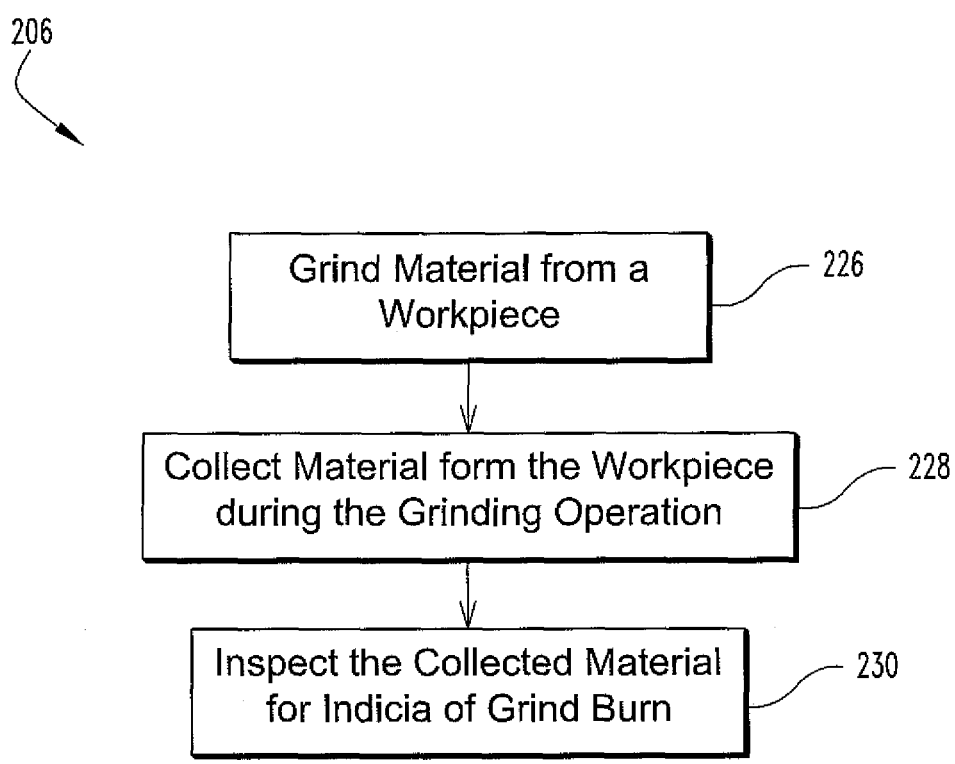
FIG. 2C is a flowchart of an embodiment of a swarf analysis process
Figure 7:
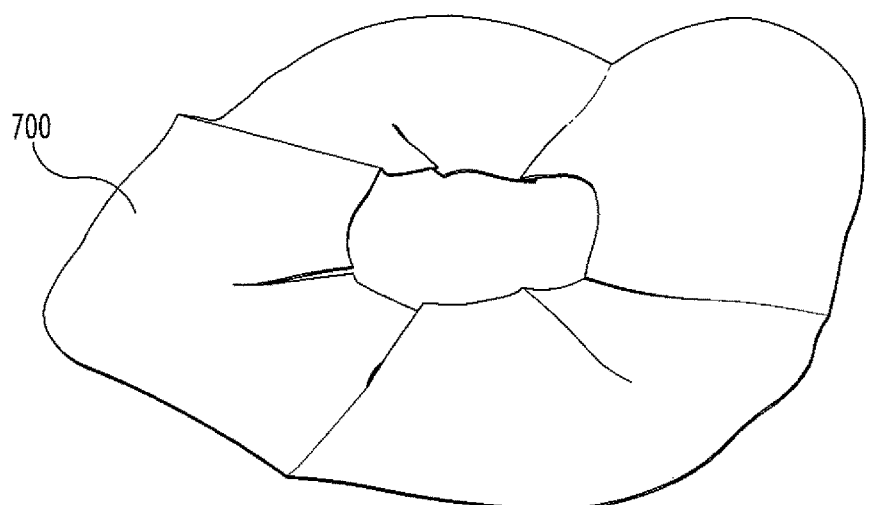
FIG. 7 is a perspective view of an embodiment of filter paper.
Figure 8:
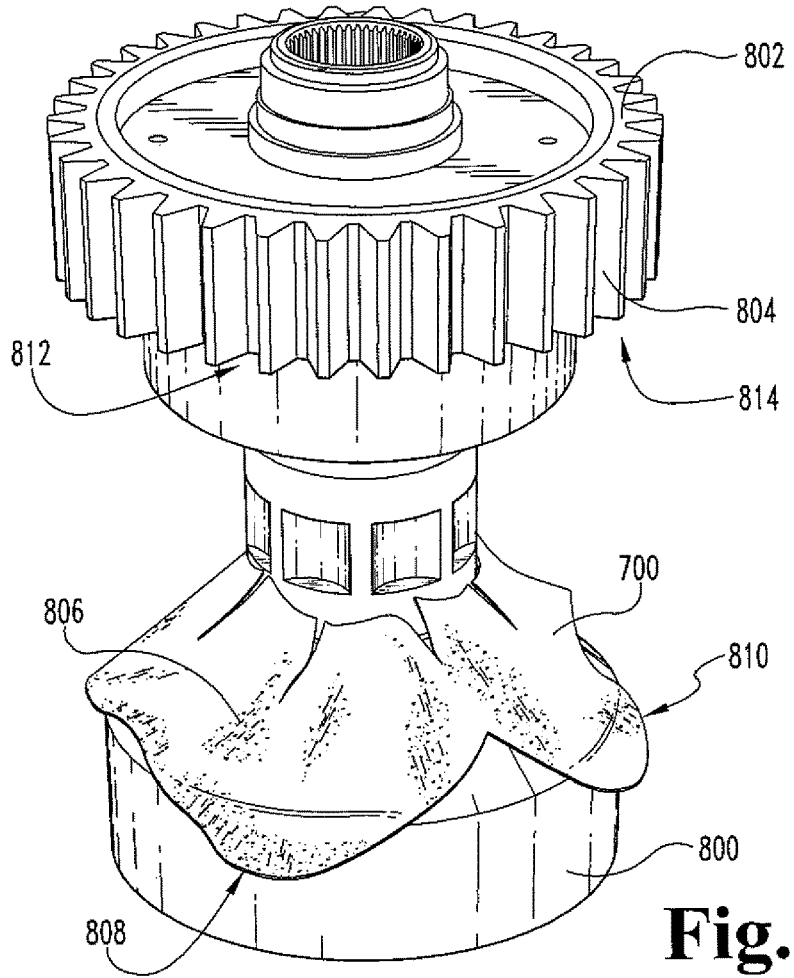
FIG. 8 is a perspective view of filter paper positioned on a gear holder for collecting swarf during a grinding operation.

In FIG. 2C, another embodiment of a method is provided for detecting and/or preventing grind burns from forming on a workpiece during a grinding operation. A swarf analysis process 206 can detect and/or prevent grind burns by analyzing the swarf produced during the grinding operation. Swarf is referred to as the material removed by a cutting or grinding operation. Before the swarf can be analyzed, it must first be collected during the grinding operation. One skilled in the art can appreciate the many ways swarf can be collected. In one aspect, the swarf can be collected by a magnet. In a different aspect, filter paper 700 can be used as illustrated in FIGS. 7 and 8. Filter paper is a semi-permeable paper barrier that is typically used for separating fine solids from liquids or air.

In the setup illustrated in FIG. 8, the filter paper 700 is positioned at the base of a workpiece holder 800. The filter paper 700 is spread around the circumference of the base and is disposed beneath a gear 802 which is coupled to the holder 800. The workpiece holder 800 is able to rotate 360° so that the entire gear can be ground. In block 226 of FIG. 2C, a gear tooth 804 of the gear 802 is ground by a grinding machine (not shown). During the grinding operation, swarf 806 is produced. As the swarf 806 is produced, it falls onto and is collected by the filter paper 700 (block 228 in FIG. 2C). With reference to block 230, after the grinding operation, the collected swarf 806 is inspected for indicia of grind burn.

Since the workpiece holder 800 is able to rotate 360°, both the gear 802 and filter paper 700 also rotate the same distance. Therefore, when a gear tooth 804 at the location 814 of the gear 802 is ground, swarf 806 is collected at or near location 810 of the filter paper. In this embodiment, location 814 is disposed almost directly above location 810 of the filter paper 700. Similarly, when a gear tooth 804 at location 812 of the gear 802 is ground, swarf 806 is collected at location 808 of the filter paper 700. Again, location 812 of the gear is disposed almost directly above location 808 of the filter paper 700. Thus, when a piece of swarf 806 is inspected from location 808 of the filter paper 700, the inspector is able to correlate the location of the filter paper 700 with the location along the gear 802 from which the swarf came. While this is a general and non-limiting example of how collected swarf is linked to the gear tooth from which it is removed, other processes known to the skilled artisan can be used.

In FIG. 9, one example of how the swarf 806 is inspected in block 230 is shown. A camera or microscope 900 having a base 904, a lens 902, and several user controls 906 can be used for the inspection. An example of such a camera 900 is a Keyence Digital Microscope VHX 100 from Keyence Corporation, Itasca, Ill. The camera should include a high magnification feature so that swarf 806 can be analyzed up to 100×, or more advantageously at about 173×. Indicia of grind burns can include changes in color and/or thickness in the collected swarf 806. For example, a gear tooth that has a grind burn can have a dark gray, blue, or black appearance, whereas a gear tooth free of grind burns will have a light gray or light brown appearance. The thickness of collected swarf does relate to the grinding force, and therefore a chip thickness that exceeds a predetermined maximum thickness threshold would indicate a change or problem in the grinding process. The threshold can be determined, for example, by mathematical modeling as described in an article entitled "Grinding Force and Power Modeling based on Chip Thickness Analysis" by Rogelio Hecker et al. in *The International Journal of Advanced Manufacturing Technology*, Vol. 33, Nos. 5-6, June 2007. If an inspection identifies that there is a grind burn on a gear tooth, the inspector is able to correlate the location of the collected swarf with the location on the gear from where the swarf was removed. Further inspection and analysis of the gear can then determine whether there is any grind burn and, if so, the severity of the grind burn. The swarf analysis process 206 therefore provides another means for detecting and/or preventing grind burns.

In an advantageous process control method 100, grind burns are detected and/or prevented by performing the acoustic emission process 202, the eddy current testing process 204, and the swarf analysis process 206. Rather than performing only one of the detection and/or prevention methods, each gear or workpiece that is ground on a grinding machine is analyzed and monitored for possible grind burn. In this embodiment, the acoustic emission process 202 monitors and detects grind burns during a grinding operation. After the grinding operation, swarf that is collected during the grinding operation is then analyzed under a camera or microscope as described above.

The swarf analysis process 206 can be performed regardless of whether the acoustic emission process 202 detected potential grind burns. As such, the swarf analysis process 206 provides an additional safety net to enhance the quality of parts being manufactured. Moreover, each part being manufactured is tested and analyzed, which provides advantages over conventional detection methods. In particular, if grind burns are detected using either the acoustic emission process 202 or swarf analysis process 206, the entire process control method 100 can be further analyzed to determine whether there are problems in the material of the workpiece, grinding wheel, etc. Since conventional detection methods are unable to provide real-time feedback, many additional defective parts are made before a problem is identified and changes can be implemented in the process control method.

In addition, the eddy current testing process 204 further identifies opportunities or conditions favorable for producing grind burns by analyzing the grinding wheel after the grinding operation. Therefore, this embodiment which includes the acoustic emission process 202, the eddy current testing process 204, and the swarf analysis process 206 provides the most complete and effective means for detecting and/or preventing grind burns from forming on a ground gear or workpiece.

While exemplary embodiments incorporating the principles of the present disclosure have been disclosed hereinabove, the present disclosure is not limited to the disclosed embodiments. Instead, this application is intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A method of detecting grind burn on an object being ground, comprising:
   removing material from an object with a grinding machine during a grinding operation;
   collecting the removed material from the object with an element during the grinding operation;

using an instrument having a lens to inspect the collected removed material for an indication of grind burn;

identifying a grind burn when the indication is a discoloration of the collected removed material or a change in thickness of the collected removed material;

and wherein, when a grind burn is identified by the identifying step, adjusting one or more parameters of the grinding machine during the grinding operation to eliminate the identified grind burn and then repeating the collecting step, the using an instrument step and the identifying step.

2. The method of claim 1, wherein the indication is substantially dark gray, blue, or black.

3. The method of claim 1, wherein the element comprises filter paper or a magnet, wherein the filter paper or magnet is fixed with respect to the object to determine the location of the grind burn based on the location of the collected removed material on the paper or magnet.

4. The method of claim 3, further comprising placing filter paper near the object.

5. The method of claim 3, wherein the filter paper is placed substantially beneath the object.

6. The method of claim 3, further comprising aligning the filter paper with the object to collect the removed material resulting from the collecting step.

7. The method of claim 6, further comprising identifying a location of the grind burn on the object from which the material is removed based on a location of the collected material on the filter paper.

8. The method of claim 1, wherein the instrument is a camera.

9. The method of claim 8, further comprising magnifying the collected removed material to inspect for the indication.

10. The method of claim 1, wherein the change in thickness is an increase in thickness of the collected removed material.

11. The method of claim 1, further comprising generating an automated warning signal when grind burn is identified.

12. The method of claim 1, wherein the identifying a grind burn includes identifying grind burn when the indication is the discoloration of the collected removed material and the change in thickness of the collected removed material.

13. The method of claim 1, wherein the identifying a grind burn includes identifying a grind burn when the indication is only the change in thickness of the collected removed material.

* * * * *